US008597350B2

(12) United States Patent
Rudser et al.

(10) Patent No.: US 8,597,350 B2
(45) Date of Patent: Dec. 3, 2013

(54) CONTROLLER AND POWER SOURCE FOR IMPLANTABLE BLOOD PUMP

(75) Inventors: John Rudser, Westwood, MA (US); Jeffrey A. LaRose, Parkland, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 13/314,875

(22) Filed: Dec. 8, 2011

(65) Prior Publication Data
US 2012/0226350 A1  Sep. 6, 2012

Related U.S. Application Data

(60) Provisional application No. 61/421,557, filed on Dec. 9, 2010.

(51) Int. Cl.
*A61M 1/10* (2006.01)
(52) U.S. Cl.
USPC ............................ 623/3.27; 623/3.1; 623/3.28
(58) Field of Classification Search
USPC ........................................ 623/3.28, 3.1, 3.27
See application file for complete search history.

(56) References Cited

U.S. PATENT DOCUMENTS

| | | |
|---|---|---|
| 2001/0037093 A1 | 11/2001 | Benkowski et al. |
| 2004/0172090 A1 | 9/2004 | Janzig et al. |
| 2008/0033500 A1 | 2/2008 | Strother et al. |
| 2008/0249591 A1 | 10/2008 | Gaw et al. |
| 2010/0130809 A1 | 5/2010 | Morello |

OTHER PUBLICATIONS

International Search Report issued by the International Searching Authority (ISA/US) on Apr. 17, 2012 in connection with International Application No. PCT/US2011/63949.
Written Opinion of the International Searching Authority issued by the International Searching Authority (ISA/US) on Apr. 17, 2012 in connection with International Application No. PCT/US2011/63949.
Notification Concerning Transmittal of International Preliminary Report on Patentability (Chapter I of the Patent Cooperation Treaty), including an International Preliminary Report on Patentability and Written Opinion of the International Searching Authority, mailed Jun. 20, 2013 by the International Bureau of WIPO in connection with PCT International Application No. PCT/US2011/063949, filed Dec. 8, 2011.

*Primary Examiner* — Thomas J Sweet
*Assistant Examiner* — Matthew Schall
(74) *Attorney, Agent, or Firm* — John P. White; Cooper & Dunham LLP

(57) ABSTRACT

Methods and apparatus for controlling the operation of, and providing power for and to, implantable ventricular assist devices which includes a pump employing a brushless DC motor-driven blood pump, are disclosed. In one embodiment, a control system for driving an implantable blood pump is provided. The digital processor is responsive to data associated with the operation of the pump received at the data transfer pump, and from program data stored in the memory, (i) to determine therefrom, the identity of the pump, (ii) to determine therefrom, electrical characteristics and features of the identified pump, and (iii) to adaptively generate and apply to the data port, control signals for driving the identified pump.

21 Claims, 5 Drawing Sheets

BLUE or WHITE
Situation Good

YELLOW
Alarm Condition

YELLOW
Alarm Condition

RED
Situation Requires
Immediate Attention

CONTROLLER AND POWER SOURCE FOR IMPLANTABLE BLOOD PUMP

REFERENCE TO RELATED APPLICATION

This application claims the benefit of U.S. Provisional Patent Application No. 61/421,557, filed Dec. 9, 2010, the disclosure of which is incorporated herein by reference in its entirety.

FIELD OF THE INVENTION

This invention relates to the field of implantable medical devices. In particular, this invention is drawn to controllers and power supplies for motor-driven implantable medical device applications.

BACKGROUND OF THE INVENTION

Implantable medical devices, such as ventricular assist devices, are being developed for long term treatment of chronic heart failure. Such devices require a pumping mechanism to move blood. Due to the nature of the application, the pumping mechanism must be highly reliable. Patient comfort is also a significant consideration.

Electrically powered pumping mechanisms typically rely on a motor such as a brushless DC motor. Brushless DC motors offer maintenance advantages in implant applications due to the lack of wear-prone brushes. Due to the lack of these electro and mechanical commutation components, commutation is generally provided electrically by drive electronics.

A prior art HeartWare Ventricular Assist System, manufactured by HeartWare Inc, Framingham Mass., is an example of an implantable ventricular assist device. At the core of the HeartWare Ventricular Assist System is a small implantable centrifugal blood pump called a HVAD® pump employing a brushless DC motor.

When implanted in a patient in a typical scenario, the pump draws blood from the left ventricle and propels that blood through an outflow graft connected to the patient's ascending aorta. The device is capable of generating up to 10 liters of blood flow per minute. With a displaced volume of only 50 cc, the HVAD pump is suitable for implantation in the pericardial space, directly adjacent to the heart. Implantation above the diaphragm leads to relatively short surgery time and quick recovery.

The HVAD pump has only one moving part, an impeller, which spins at a rate between 1800 and 4000 revolutions per minute. The impeller is suspended within the pump housing through a combination of passive magnets and hydrodynamic thrust bearings. This hydrodynamic suspension is achieved by a gentle incline on the upper surfaces of the impeller blades. When the impeller spins, blood flows across these inclined surfaces, creating a "cushion" between the impeller and the pump housing. There are no mechanical bearings or any points of contact between the impeller and the pump housing.

Device reliability is enhanced through the use of dual motor stators with independent drive circuitry, allowing a seamless transition between dual and single stator mode if required. The pump's inflow cannula is integrated with the device, and surgically implanted into the heart's ventricle. This proximity is expected to facilitate ease of implant and to help ensure optimal blood flow characteristics. The use of a wide-bladed impeller and clear flow paths through the system minimizes risk of pump-induced hemolysis (damage to blood cells) or thrombus (blood clotting).

Typically, while the pump is implanted in the patient, a controller and the drive electronics for the pump, and other control subsystems for the pump, including the power supply, are located outside the patient, for example, in a control/power supply module tethered by a transcutaneous electrical cable, to the implanted pump of the overall HeartWare Ventricular Assist System For the HeartWare Ventricular Assist System, an external (to the patient) controller includes the drive electronics for the pump (coupled directly to the windings of the motor) and provides drive and control signals to the pump. The controller also provides feedback and alarms to the patient regarding the operation of the device. Commutation control for the brushless DC motors is effected by the controller and the drive electronics, in a feedback manner. The controller provides a commutation control signal for a selected phase of the motor in accordance with a sampled back-emf voltage of that phase (sensed via the tether cable). The back-emf is sampled only while the corresponding selected phase drive voltage is substantially zero. The frequency of the brushless DC drive voltage is varied in accordance with the commutation control signal. In one form, the back-emf is normalized with respect to a commanded rotor angular velocity. A speed control generates a speed control signal corresponding to a difference between a commanded angular velocity and an angular velocity inferred from the frequency of the drive voltage.

A redundant power supply is provided by two batteries, or one battery and an AC adapter or DC adapter. The redundant power supply provides power for the controller, and particularly the drive electronics. When the battery is depleted (for example, after approximately 6 hours), the controller automatically switches to the standby power source, battery or adapter, and the depleted battery is replaced.

A "Patient Pack" assembly includes a carrying case that holds the controller and power source(s). The case can be adapted to be carried over the patient's shoulder or worn around the patient's waist.

While the prior art HeartWare Ventricular Assist System, in the aggregate, performs the desired ventricular assist functions required for long term treatment of chronic heart failure, there is a need for improved subsystems and subassemblies which would provide enhanced blood flow results and improved patient-convenience features, easing the maintenance burden on the patient, thereby providing an improved quality of life.

SUMMARY OF THE INVENTION

Improved methods and apparatus for controlling the operation of, and providing power for and to, implantable ventricular assist devices which include a pump employing a brushless DC motor-driven blood pump, are disclosed.

In one embodiment, a control system for driving an implantable blood pump is provided. The pump is characterized by a set of electrical characteristics and features. The pump includes a pump power port for receiving pump drive signals for driving the pump, and includes a pump data port for receiving and transmitting data associated with the operation of the pump. In one form, such data is at least in part, analog, provided by the back-emf available on direct connections to the motor windings.

The control system comprises a controller including a housing disposed about an interior region, a digital processor and associated memory, an electrical power output port, a data transfer port, a data conductor assembly, and an electrical power conductor assembly. The data transfer port and the data transfer port extend through the housing. The digital processor and associated memory, the power supply support structure, the power supply support structure, and the electrical power conductor assembly are disposed within the interior region.

The memory includes information stored therein, wherein the stored information is representative of a program for controlling operation of the pump. The memory in some forms, also stores data representative of various parameters of a connected pump detected during use, and/or maintains historical data representative of pump performance and/or operating conditions.

The electrical power output port is adapted for transmitting pump drive signals to the pump. In some forms, where a pump includes circuitry, electrical power is transferred to the pump via the electrical power output port.

The data transfer port is adapted for transmitting and receiving data associated with the operation of the pump. The data conductor assembly is associated with the data transfer port, and is adapted for coupling data associated with the operation of the pump between the digital processor and the data port.

The digital processor is responsive to data associated with the operation of the pump received at the data transfer pump, and from program data stored in the memory:
  i. to determine therefrom, the identity of the pump,
  ii. to determine therefrom, electrical characteristics and features of the identified pump, and
  iii. to adaptively generate and apply to the data port, control signals for driving the identified pump.

In an embodiment, the power output port and the data transfer port are disposed within a single controller connector assembly.

In a form for use with a pump having the pump power port and the pump data port disposed within a single pump connector assembly, an elongated flexible electrical cable is included, which extends from a controller end of the cable to a pump end of the cable. The cable has a controller-end connector at the controller end and a pump-end connector at the pump end. The controller-end connector is adapted to mate with the controller connector assembly of the housing and the pump-end connector is adapted to mate with the pump connector assembly on the pump. When the connectors are so mated, power drive signals can pass between the power output port and the pump power port, and data can pass between the data transfer port and the pump data port. In a preferred form, the flexible electrical cable includes a flexible helical-formed strain relief segment.

In an embodiment, the housing extends along a housing axis between a top end of the housing and a bottom end of the housing. At the top end, the housing includes a top panel having an outer circumferential top boundary and extending transverse to the housing axis. At the bottom end, the housing includes a bottom panel having an outer circumferential bottom boundary and extending transverse to the housing axis.

The housing includes a tube, or tube-like, structure comprising a set of contiguous lateral panels disposed about and extending along the housing axis, from the top circumferential boundary of the top panel to the bottom circumferential boundary of the bottom panel, so that the top panel, the bottom panel and the tube enclose the interior region. An outermost surface of the top panel is substantially planar. The tube includes first and second opposing portions, wherein an outermost surface of the first opposing portion is substantially planar and an outermost surface of the second opposing portion is substantially planar.

In a form, the digital processor of the control system is configured to selectively operative to generate a time-remaining (TR) signal having a value corresponding to a calculated remaining time of operation the control system under power from a battery installed in the battery support structure, wherein the value is determined from a measure of a current state of charge of the battery and an expected load/current drawdown pursuant to program data stored in the memory in association with the pump.

In a preferred form, a first display device is disposed on a planar outermost surface of the top panel. An associated first display conductor assembly is disposed within the interior region for electrically coupling the first display device to the digital processor. Again, in a preferred form, the digital processor controls the first data device to selectively display data representative of the time-remaining (TR) signal, and general or summary of the state of the pump, controller, and power source(s).

In a preferred form, a second display device is disposed on a planar outermost surface of the side panel. An associated display conductor assembly is disposed within the interior region for electrically coupling the second display device to the digital processor. Again, in a preferred form, the digital processor controls the second data device to selectively display data representative of the time-remaining (TR) signal, details for the pump flow, power, and speed. Navigation through the user interface provides detailed logging of alarms/alerts, events, and data.

27a—Through the use of color, the display indicates: all is well, alerts, and alarm conditions.

In various forms, the first display and the second display may further include integrated switches, such as membrane switches, underlying at least a part of portions of the display, so that a user and/or administrators can input information to the digital processor.

In a form, the tube is split, thereby defining a circumferential boundary between the top panel and the bottom panel, so that an upper cup-like portion including the top panel and portions of the tube extending therefrom is defined, and a lower cup-like portion including the bottom panel and portions of the tube extending therefrom is defined.

In this form, the power supply support assembly is disposed in the interior region bounded by the lower cup-like portion, and the digital processor and associated memory is disposed in the interior region bounded by the upper cup-like portion. The second display device is disposed on the outermost surface of the upper cup-like portion. A coupler assembly is provided for reversibly attaching the upper cup-like portion to the lower cup-like portion. The power supply structure can provide an independent means of displaying level of charge.

Preferably, the power supply support structure includes a coupler adapted for receiving power from a source external to the housing. More preferably, the power supply support structure is a coupler adapted for supporting a battery in the interior region, and most preferably, the power supply support structure is shaped to receive a battery having a predetermined exterior shape, and to guide movement of the battery during insertion thereof. Preferably, the guide structure and the battery shape are keyed so that a user can only insert the battery in a correct position.

In a preferred form, information stored in the memory is representative of a plurality of programs, wherein each program for controlling operation of a particular pump. In this form, the digital processor is responsive to data associated with the operation of the pump received at the data transfer pump, and from program data stored in the memory,
  i. to determine therefrom, the identity of the particular pump, ii. to determine therefrom, electrical characteristics and features of the identified particular pump, and iii. to adaptively generate and apply to the data port, control signals for driving the identified particular pump.

In a form, the controller includes a battery in the power supply support structure, whereby power for the components in the control system is provided, including power for generating the pump drive signals applied to the electrical power output port. The digital processor is further responsive to data associated with the operation of the pump received at the data transfer port, and from program data stored in the memory, to generate therefrom, a signal representative of the amount of time remaining during which the pump can be driven, based on the state of charge of the battery and in accordance with the program for driving the pump.

Preferably, the controller further includes a display device disposed on the housing, and the digital processor is adapted to drive the display device to display a human-readable signal representative of the determined amount of time remaining during which the pump can be driven in accordance with the program.

In a form, the controller is adapted to receive a primary battery in the power supply support structure, whereby power for the pump is applied to the electrical power output port, and further includes a secondary battery disposed in the interior region, wherein the secondary battery is operative at times when the primary battery is charged below a predetermined threshold or during replacement of the primary battery.

BRIEF DESCRIPTION OF THE DRAWINGS

A more complete appreciation of the present invention and many of the attendant advantages thereof will be better understood by reference to the following detailed description when considered in connection with the accompanying drawings, wherein.

DETAILED DESCRIPTION

Figure 1:
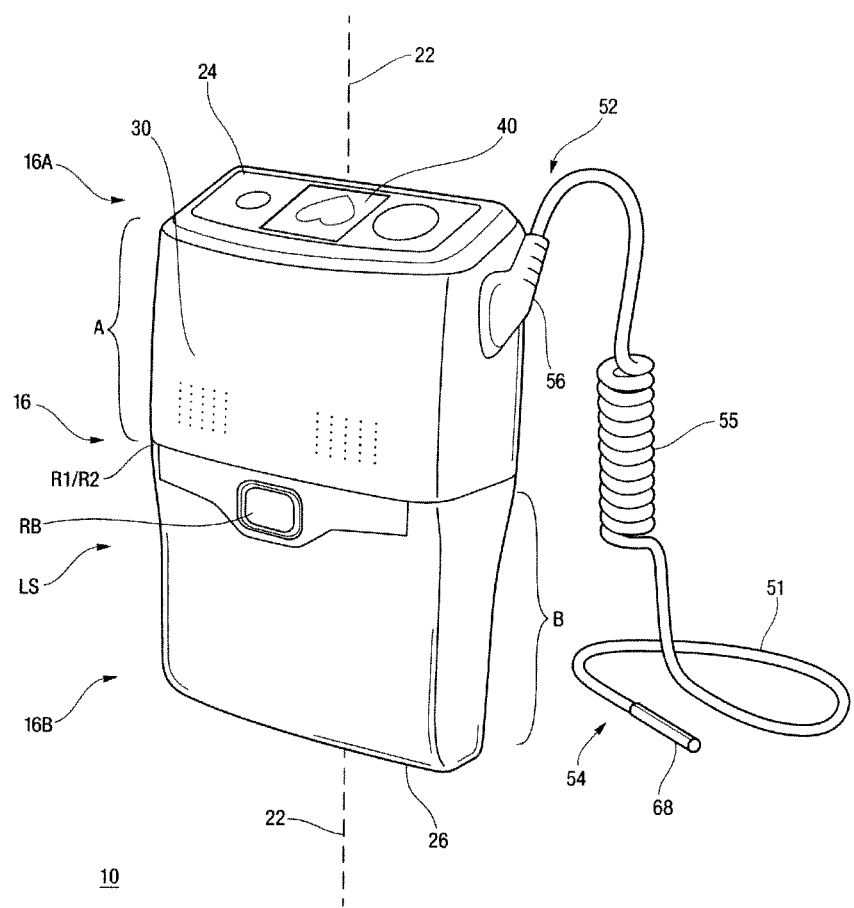
FIG. 1 is front-top-side view of a control system and connecting cable of the disclosure.

A control system 10 for controlling the operation of, and providing power for and to, implantable ventricular assist devices which include a pump employing a brushless DC motor-driven blood pump, is shown in FIGS. 1-4. The control system 10 is shown in diagrammatic form in FIG. 5, together with an exemplary pump 12.

As shown in FIGS. 1-5, the control system 10 includes a housing 16 disposed about an interior region 20. Housing 16 extends along a housing axis 22 between a top end 16A and a bottom end 16B. At the top end 16A, a top panel 24 having a substantially planar outer surface, extends transverse to the housing axis 22. At the bottom end 16B, a bottom panel 26 having a substantially planar outer surface, extends transverse to the housing axis 22. Lateral surfaces LS of housing 16 extend between the circumferential outer boundary of top panel 24 and the circumferential outer boundary of bottom panel 26. In the aggregate, the lateral surfaces of housing 16 form a tube-like structure extending along axis 22, with the end panels 24 and 26 forming closures to the tube, or tube-like, structure, enclosing the interior region 20.

The tube-like structure includes a first, or outer, portion 30 (referred to herein as "LS outer portion 30") opposite to a second, or inner, portion 32 (referred to herein as "LS inner portion 32"). Opposing uppermost portions of the outermost surfaces of LS outer portion 30 and LS inner portion 32, are substantially planar as well as substantially parallel, although as illustrated particularly in FIGS. 1-4, those portions are not precisely parallel. Different shapes and relationships may be employed in other embodiments.

A first display device 40 is disposed on the outer surface of top panel 24. A second display device 42 is disposed on the outer surface of the LS inner portion 32. The housing 16 also includes on a lateral surface, a power port 46 and a data port 48 disposed within an input/output (I/O) connector assembly 49. An input device 50 is disposed on the outer surface of LS outer portion 30.

An elongated flexible electrical cable 51 extends from a controller end 52 to a pump end 54. The cable 51 further includes a flexible, helical-shaped strain relief segment 55 (shown in FIGS. 1-3) between the cable ends 52 and 54 A controller-end connector assembly 56 is disposed at the controller end 52, and a pump end connector assembly 60 is disposed at the pump end 54 of cable 55. The connector assembly 56 includes connector portions 46' and 48' adapted to mate with the power port 46 and the data port 48, respectively, of the I/O connector assembly 49.

The pump end connector assembly 60 similarly includes connector portions 62' and 64' adapted to mate with a pump power port 62 and pump data port 64 of a pump I/O connector assembly 68.

The controller-end connector assembly 56 is adapted to mate with an I/O connector assembly 49 on the housing 16, and the pump-end connector assembly 60 is adapted mate with the pump connector assembly 68 on the pump 12.

When the controller end connector assembly 56 is connected to the I/O connector assembly 49 of the controller 10, and the pump end connector assembly 60 is connected to the pump I/O connector assembly 68 of the pump 12, pump drive signals can pass between the power output port 46 and the pump power port 62. Data can pass between the data transfer port 48 and the pump data port 64, making available to data processor 32, the real-time impedances of the windings of the motor of pump 12.

In the illustrated embodiment, the housing is split into two opposed cup-like components: cup-like upper housing portion A having a circumferential rim R1, and cup-like lower housing portion B having a circumferential rim R2. Rim R1 of the upper housing portion A is adapted to interfit with and reversibly couple to the rim R2 of the lower housing portion B. A latch assembly enables the quick release of housing portion A from or to lower housing portion B, in response to depression of a release button RB disposed on the LS outer portion 30 of upper housing portion A (and an associated latch assembly, not shown). Rim R1 and rim R2 are shown in FIG. 1 by the reference symbol "R1/R2", and in FIG. 5, rim R1 and rim R2 are depicted as adjacent dashed lines extending across housing 16.

Figure 5:
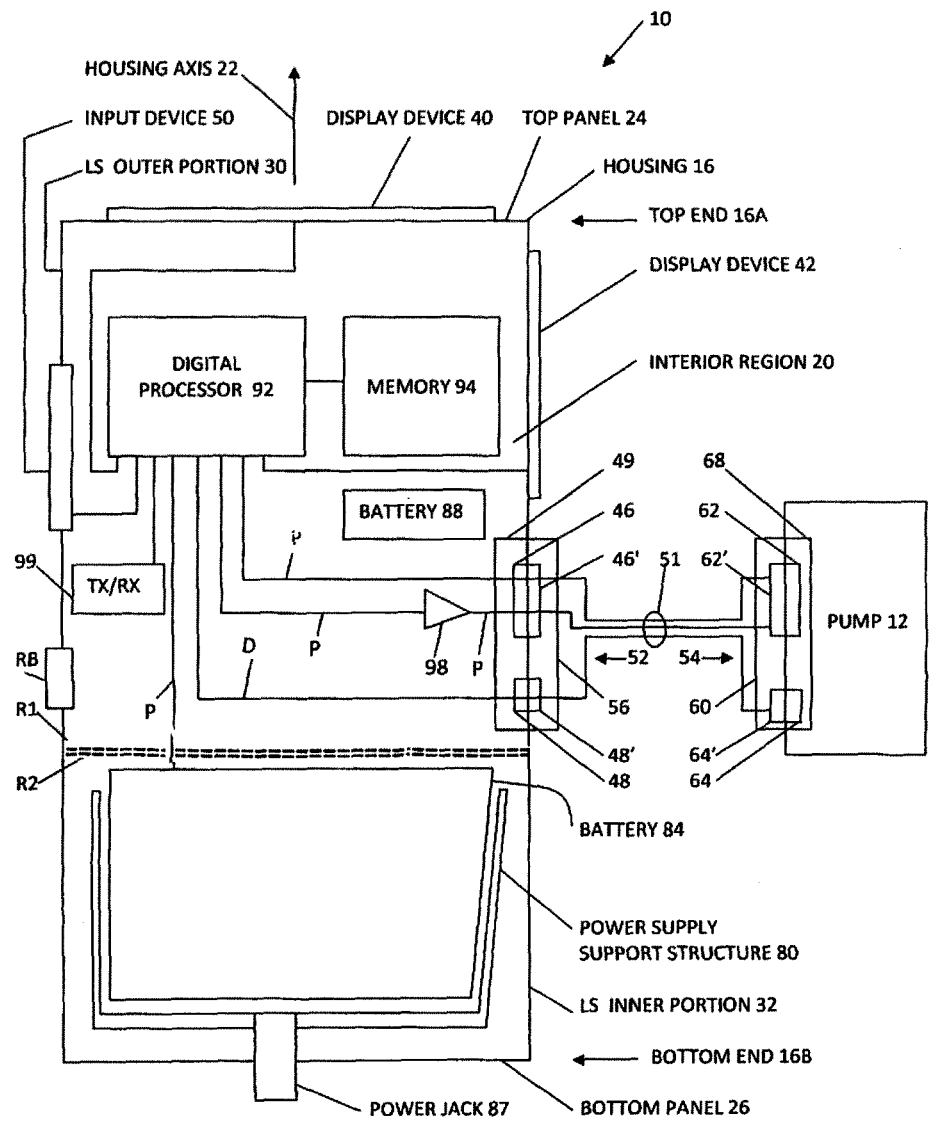
FIG. 5 is a diagrammatic representation of the control system and connecting cable of FIG. 1, together with an exemplary pump.

In the illustrated embodiment, the cup-like housing portion B provides electrical power for the operation of control system 10. As shown in FIG. 5, housing portion B includes in its interior, a power supply support structure 80. The support structure 80 has a cup-like form adapted to receive a battery 84 in its interior region. In some forms of the control system 10, the battery 84 is affixed to housing portion B and the portion B/battery module is replaceable as a unit. In other forms, the battery 84 is removably located in housing portion B, and is user-replaceable within housing portion B. In the illustrated form of FIG. 5, the interior of the power supply support structure 80 is geometrically keyed to the shape of the battery 84, to aid a user in replacing the battery in a fail-safe manner. In that structure, both the support structure 80 and the battery 84 are shown with geometric shape keying so that the battery 84 can only be inserted in support structure 80 in a single, proper manner. A secondary, or back-up, battery 88 is disposed within the interior of upper housing portion A, and is coupled to the various elements in control system 10, to provide back-up power to control system 10 in the event of catastrophic failure of battery 84 or during routine replacement of battery 84 with a charged or fresh unit.

As shown in FIG. 5 of the illustrated embodiment, the support structure 80 also includes power jack 87 so that the control system 10 can be powered by an external power source.

In the illustrated embodiment, the cup-like housing portion A houses the components which provide functional operation of control system 10, as it relates to the driving of an implanted pump 12. The housing portion A houses a digital signal processor 92 and an associated memory 94, a pump drive network 98, and, as noted above the secondary battery 88, as well as cabling which interconnects the various elements in the control system 10.

An electrical power conductor assembly P is disposed within interior region 20. That electrical power conductor assembly P is associated with the power supply support structure 80, and couples electrical power from a power supply (whether it be from a battery 84 disposed in support structure 80, from an external source by way of power jack 87 or from secondary battery 88), and provides electrical power to all elements in the control system 10. In addition, the electrical power conductor assembly P provides a power drive signal line from the digital processor 92, by way of a power amplifier 98, to the electrical power output port 46, where that power drive signal can be coupled via cable 51 to the motor (not shown) of pump 12.

A data conductor assembly D also is disposed within interior region 20. That data conductor assembly D. The data conductor assembly D provides analog "data" representative of the current state of the motor of pump 12, received via cable 51 at data transfer port 48, to the digital processor 92. In one form, that analog "data" is provided as a direct line to the windings of the motor of pump 12, from which the digital processor determines the impedance as a function of time of the respective windings of the motor. In response to that "impedance" data, the digital processor determines the appropriate drive power signal to be applied by way of power port 46 and cable 51, to the motor The input device 50 in some forms, includes a keyboard, and in other forms includes a connector, and in still other forms, includes both. Through the input device 50, a user of, or administrator for, the control system 10 can activate or deactivate the system 10, or can add, modify or delete any information associated with the operation of the system 10, for example by modifying the information stored in memory 94.

The control system 10 is adapted for use by an ambulatory patient who has an implanted blood pump. Under control of system 10, the patient's pump performs as programmed. For convenience, the patient can wear the control system 10 in a holster-like support extending about his or her waist, with the housing axis 22 substantially vertical and the LS inner portion against the patient's body. With this configuration, the patient can conveniently view the display device 40 on top panel 24, without removing control system 10 from the holster. An administrator, for example, a physician or nurse, who might hold the system 10 after removing it from the patient's holster, can view either display device 40 or display device 42 on LS inner portion 32. In the illustrated form, display 42 is relatively large compared to display device 40, so that more complex information can be displayed to the administrator while relatively simple, albeit highly useful, information can be displayed to the patient.

The memory 94 stores program information, for example, for controlling the operation of one of a number of (same or different model) implantable blood pumps which might be connected to, and driven by, the system 10. The digital processor 92 is adapted to run and control the overall system 10 as well as a pump attached thereto via cable 51. Display 42 is driven by the processor 92 to selectively display information which is generally useful to an administrator of a pump 12, such as a nurse or physician.

In operation, the control system 10, when deployed, is coupled by way of cable 51 to a pump 12. Pursuant to its supervisory program from the memory 94, the system 10 determines from a coupled pump 12, the identity of the pump, for example the manufacturer and model number, the serial number, and in some cases the identity of the patient associated with the pump. From that determined identity information, system 10 determines certain electrical characteristics and features of the identified pump, and in some cases related to the patient associated with the pump. System 10 then adaptively generates and applies by way of the power port 46, control signals (i.e., pump drive signals) for driving the identified pump 12. As noted above, in the illustrated embodiment, the system 10 effectively monitors in real time, the operation of the pump 12, based on the impedance of the windings of the pump's motor, and generates appropriate time-based pump drive signals for application to those windings, to achieve the performance defined by the pump's program (which may be customized to the patient) stored in memory 94.

In one form, system 10 is adapted to control operation of one of a number of pumps of the same model, and the program information stored in memory 94 defines the features and modes of operation of the identified pump. In some cases this information is customized on a patient by patient basis, for each of a number of prospective pumps. In another form, system 10 is adapted to control operation of all of a number of different types of pumps. Similar control information is provided for each such pump in memory 94. In some cases, the pumps-to-be-controlled are relatively passive, and provide information back to the control system 10 in the form of signal lines coupled to the windings of the pump motor, so that impedances can be detected and drive signals generated accordingly. In other cases, the pumps-to-be-controlled, are active, and provide over data port 48, data representative of various conditions in the pump, for example, identified faults, or data representative of certain conditions, such as indications of the occurrence of bases for an imminent failure of the pump. Among the various determinations made, system 10 generates a signal representative of the time remaining of operation under battery power, for the specific battery then installed, taking into consideration of the current state of charge and expected load/current drawdown. That time-remaining signal is selectively displayed on one, or both, of display devices 40 and 42, in human-readable form. The time-remaining value is based in part on the drive program associated with the pump, so as to provide a highly accurate reading all of the time remaining. When the time-remaining value reaches a threshold or range indicative of danger to the patient, an alarm is generated for example an audible alarm, a vibratory alarm, and a light alarm, solid or flashing.

Figure 3A:
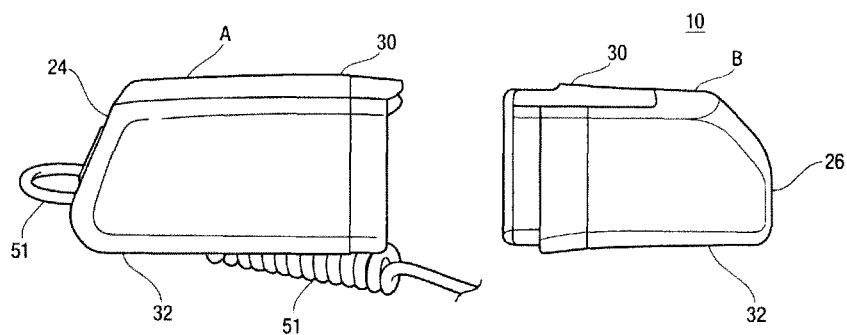
FIG. 3A and FIG. 3B are side views of the control system and connecting cable of FIG. 1, showing a battery-containing portion detached from a processor-containing portion, and the battery-containing portion attached to the processor-containing portion, respectively.
Figure 3B:
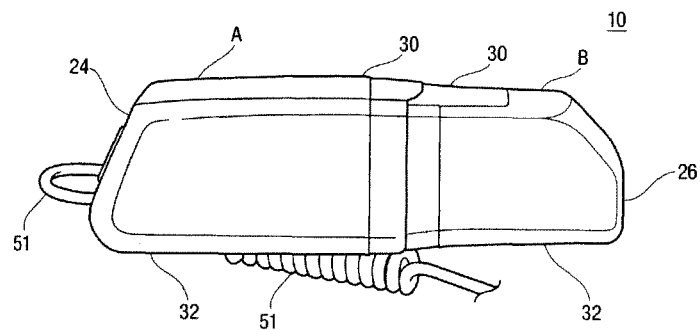

As noted above, the battery-containing lower cup-like portion B of housing 16 can be separated from the upper cup-like portion A (by depressing button RB), and a replacement lower cup-portion B with a fresh, fully charged battery, can replace the removed portion. A side view of the control system 10 is shown in FIG. 3A (with lower portion B of housing 16 attached to upper portion A of housing 16) and FIG. 3B (with lower portion B removed and displaced from upper portion A.

Also included within the housing 16, is a wireless transmitter/receiver TX/RX. At transmitter is coupled to the digital processor 92 and is adapted to selectively transmit and receive data. By way of example, the transmitted data may be representative of indicia of operation of a pump 12 under the control of system 10, to a main processor. The information can be selected to include data representative of broad aspects of the operation of the connected pump, such as pump activity, fault conditions, warning/alarm conditions and other data necessary for comprehensive logs for the pump. The received data, by way of example, may be program or control instructions, or modification, for use in the control of system 10, and in turn, a pump attached thereto. In various forms, the control system 10 may include only a transmitter, or only a receiver, rather than the transmitter/receiver in the illustrated embodiment.

Figure 2:
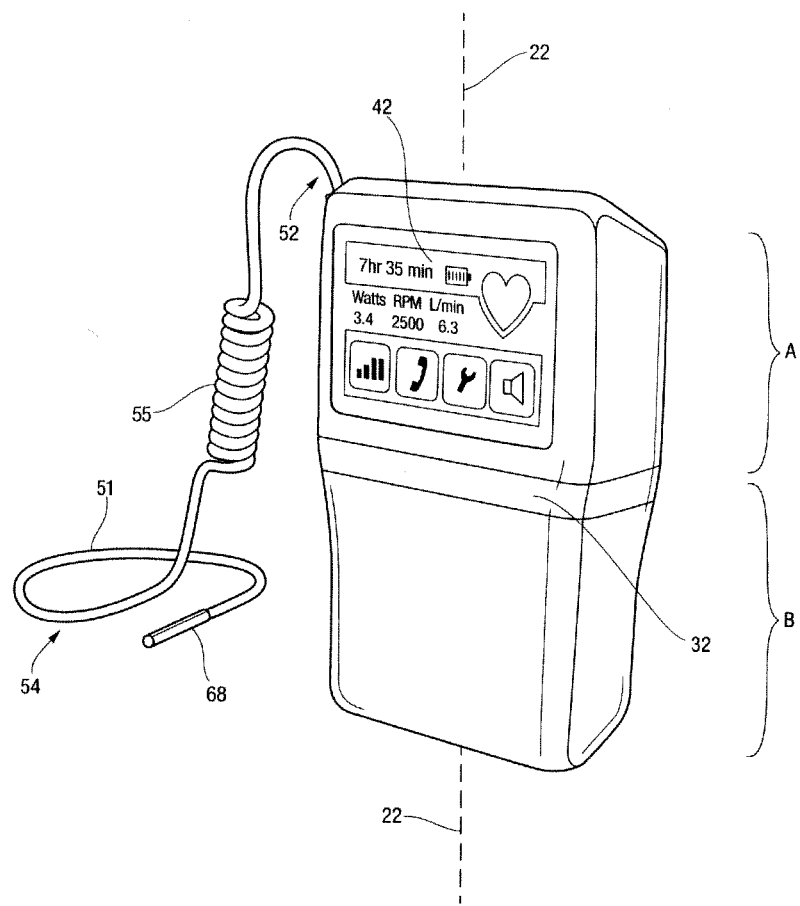
FIG. 2 is partially rear-side view of the control system and connecting cable of FIG. 1.

An exemplary set of information displayed on display device 42, is shown in FIG. 2. The data shown primarily in the form of icons or indicia. Indicia representative of length of time remaining for operation at the current state of battery 84 (7 hours, 35 min.), battery life, characteristics of the pump attached to the system 10 (power being dissipated,=3.4 Watts, pump impeller rotational rate=22000 RPM, and pump output flow rate (6.3 Liters per minute), are all illustrated in FIG. 2. In addition, there is an icon overlying a membrane switch that can bring up data representative of signal strength relevant to the receiver RX, an icon in the shape of a telephone handset overlying a membrane switch that can initiate a telephone call, an icon in the shape of a wrench which overlying a membrane switch that can initiate a tool or setting screen, and an icon in the shape of loudspeaker overlying a membrane switch that can bring up a audio volume control screen. In addition, there is a condition (of control system 10) indicator, which in FIG. 2 is a heart-shaped icon that is indicative of "proper operation" of the pump of a patient connected to the system 10. An alternative icon for the condition indicator is shown in FIG. 4D. The aforementioned data displayed on display device 42 is primarily of value to an administrator, such as a physician or nurse. 42

Figure 4A:
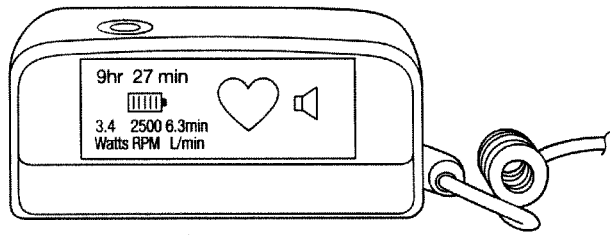
FIG. 4A-FIG 4D show top views of the top panel, with a display device thereon, of the control system of FIG. 1.
Figure 4B:
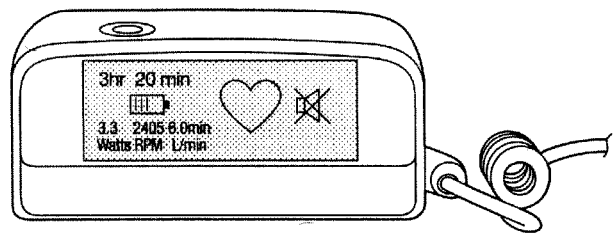
Figure 4C:
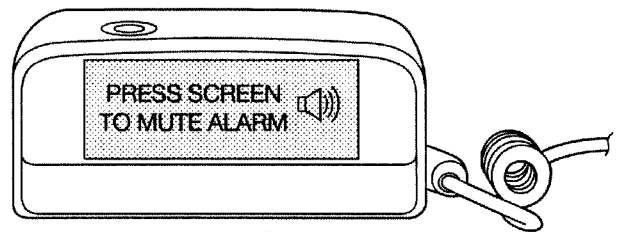
Figure 4D:
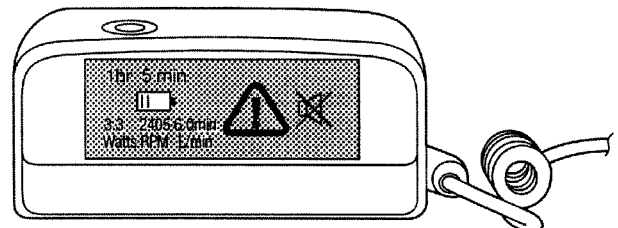

An exemplary set of information displayed on display device 4( ) is shown in FIGS. 4A-4D. The data shown in FIGS. 4A, 4B and 4D is in the form of indicia representative of length of time remaining for operation at the current state of battery 84, battery life, and characteristics of the pump attached to the system 10 (power being dissipated, pump impeller rotational rate, pump output flow rate. There also is a loudspeaker-shaped icon indicative of auditory alarms being on or off (where an "X" overlays the loudspeaker-shaped icon when alarms are "muted temporarily"). As in the illustrated display device 42 in FIG. 2, there also is an icon that is indicative of "proper operation" of the pump of a patient connected to the system 10. In FIGS. 4A and 4B, that icon is heart-shaped, indicating "proper operation", or "situation good", of the pump of a patient connected to the system 10. In FIG. 4D, the condition indicator icon is in the form of the international traffic signal for "attention", a triangle with an exclamation point in its interior. The data in display device in FIG. 4A is representative of "all is well", and has a white or blue backlight. The data in display device in FIG. 4B is representative of "alert condition", and has a yellow backlight. When control system 10 is in its "alarm condition", the display 40 alternates with that shown in FIG. 4B and that shown in FIG. 4C, with the latter displaying "PRESS SCREEN TO MUTE ALARM", with a yellow backlight. The data in display device in FIG. 4D is representative of "Situation requires immediate attention", and has a red backlight.

The backlight values (blue/white, yellow, red are qualitative indicators of great importance to the user/patient having his or her implanted blood pump under the control of the control system 10.

Although this invention has been described in terms of certain embodiments, other embodiments that are apparent to those of ordinary skill in the art, including embodiments which do not provide all of the benefits and features set forth herein, are also within the scope of this invention. Accordingly, the scope of the present invention is defined only by reference to the appended claims.

What is claimed is:

1. A control system for driving an implantable blood pump wherein the pump is characterized by a set of electrical characteristics and features, and includes a pump power port for receiving pump drive signals for driving the pump, and includes a pump data port for receiving and transmitting data associated with the operation of the pump, comprising:
   a controller including a housing disposed about an interior region, and including:
   A. a digital processor and associated memory disposed within the interior region, wherein the memory includes information stored therein, wherein the stored information includes a program for controlling operation of the pump,
   B. a power supply support structure disposed within the interior region,
   C. an electrical power output port extending through the housing, for transmitting electrical power to the pump,
   D. a data transfer port extending through the housing, for transmitting and receiving data associated with the operation of the pump,
   E. a data conductor assembly disposed within the interior region and associated with the data transfer port, for coupling data associated with the operation of the pump between the digital processor and the data port,
   F. an electrical power conductor assembly disposed within the interior region and associated with the power supply support structure, for coupling electrical power from a power supply to the digital processor and for coupling pump drive signals from the digital processor to the electrical power output port, wherein the digital processor is responsive to data associated with the operation of the pump received at the data transfer port, and to the information stored in the memory,
       i. to determine therefrom, the identity of the pump,
       ii. to determine therefrom, electrical characteristics and features of the identified pump, and
       iii. to adaptively generate and apply to the power port, pump drive signals for driving the identified pump.

2. A control system according to claim 1, wherein the power output port and the data transfer port are disposed within a single controller connector assembly.

3. A control system according to claim 2, for use with a pump having the pump power port and the pump data port disposed within a single pump connector assembly, and further comprising:
an elongated flexible electrical cable extending from a controller end to a pump end, and including a controller-end connector at the controller end and a pump-end connector at the pump end, wherein the controller-end connector is adapted to mate with the controller connector assembly and the pump-end connector is adapted to mate with the pump connector assembly, thereby when the connectors are so mated, power can pass between the power output port and the pump power port and data can pass between the data transfer port and the pump data port.

4. A control system according to claim 3, wherein the flexible electrical cable includes a flexible helical-formed strain relief segment.

5. A control system according to claim 1, wherein the housing extends along a housing axis between a top end of the housing and a bottom end of the housing,
wherein at the top end, the housing includes a top panel having an outer circumferential top boundary and extending transverse to the housing axis, and at the bottom end, the housing includes a bottom panel having an outer circumferential bottom boundary and extending transverse to the housing axis, and wherein the housing includes a tube comprising a set of contiguous lateral panels disposed about and extending along the housing axis from the top boundary of the top panel to the bottom boundary of the bottom panel, whereby the top panel, the bottom panel and the tube enclose the interior region, wherein an outermost surface of the top panel is substantially planar, wherein the tube includes first and second opposing portions, wherein an outermost surface of the first opposing portion is substantially planar and an outermost surface of the second opposing portion is substantially planar.

6. A control system according to claim 5, further comprising:
a first display device disposed on the outermost surface of the top panel, and an associated first display conductor assembly disposed within the interior region for electrically coupling the first display device to the digital processor.

7. A control system according to claim 6, wherein the digital processor is selectively operative to generate a time-remaining (TR) signal having a value corresponding to a calculated remaining time of operation the control system under power from a battery installed in the battery support structure, wherein the value is determined from a measure of a current state of charge of the battery and an expected load/current drawdown pursuant to program data stored in the memory in association with the pump.

8. A control system according to claim 6
a second display device disposed on the outermost surface of the first opposing portion, and an associated second display conductor assembly disposed within the interior region for electrically coupling the second display to the digital processor.

9. A control system according to claim 8 wherein the digital processor is selectively operative to generate a time-remaining (TR) signal having a value corresponding to a calculated remaining time of operation the control system under power from a battery installed in the battery support structure, wherein the value is determined from a measure of a current state of charge of the battery and an expected load/current drawdown pursuant to program data stored in the memory in association with the pump.

10. A control system according to claim 5, wherein the tube is split, thereby defining a circumferential boundary between the top panel and the bottom panel, thereby defining an upper cup-like portion including the top panel and portions of the tube extending therefrom and a lower cup-like portion including the bottom panel and portions of the tube extending therefrom, and
wherein
i. the power supply support assembly is disposed in the interior region bounded by the lower cup-like portion,
ii. the digital processor and associated memory is disposed in the interior region bounded by the upper cup-like portion, and
iii. the second display device is disposed on the outermost surface of the upper cup-like portion, and further comprising a coupler for reversibly attaching the upper cup-like portion to the lower cup-like portion.

11. A control system according to claim 10, wherein the power supply support structure includes a coupler adapted for receiving power from a source external to the housing.

12. A control system according to claim 10, wherein the power supply support structure is a coupler adapted for supporting a battery in the interior region.

13. A control system according to claim 12, wherein the power supply support structure is shaped to receive a battery having a predetermined exterior shape, and guide movement of the battery during insertion thereof.

14. A control system according to claim 1, wherein the stored information includes a plurality of programs, each program for controlling operation of a particular pump, and wherein the digital processor is responsive to data associated with the operation of the pump received at the data transfer port, and to the information stored in the memory,
i. to determine therefrom, the identity of the particular pump,
ii. to determine therefrom, electrical characteristics and features of the identified particular pump, and
iii. to adaptively generate and apply to the data port, control signals for driving the identified particular pump.

15. A control system according to claim 1, wherein the controller includes a battery in the power supply support structure, whereby power for the pump is applied to the electrical power output port, and
the digital processor is responsive to data associated with the operation of the pump received at the data transfer port, and from program data stored in the memory, to determine therefrom:
the amount of time remaining during which the pump can be driven in accordance with the program.

16. A control system according to claim 15, wherein the controller further includes a display device disposed on the housing, and
wherein the digital processor is adapted to drive the display device to display a human readable signal representative of the determined amount of time remaining during which the pump can be driven in accordance with the program.

17. A control system according to claim 15, wherein the digital processor is adapted to generate a human-detectable alarm when the determined amount of time remaining during which the pump can be driven in accordance with the program, equals a predetermined threshold.

18. A control system according to claim 17, wherein the alarm is one or more from the group consisting of sound, vibration and light.

19. A control system according to claim 1, wherein the controller is
adapted to receive a primary battery in the power supply support structure, whereby
power for the pump is applied to the electrical power output port, and further includes
a secondary battery disposed in the interior region, wherein the secondary battery is operative at times when the primary battery is charged below a predetermined threshold or during replacement of the primary battery.

20. A control system according to claim 7, wherein the digital processor controls a feedback device to selectively communicate data representative of the value associated with the time-remaining (TR) signal.

21. A control system according to claim 9, wherein the digital processor controls a feedback device to selectively communicate data representative of the value associated with the time-remaining (TR) signal.

* * * * *